US00PP16953P2

(12) United States Plant Patent
Pieters

(10) Patent No.: US PP16,953 P2
(45) Date of Patent: Aug. 8, 2006

(54) ***CHRYSANTHEMUM* PLANT NAMED 'GEDI THREE VER'**

(50) Latin Name: *Chrysanthemum morifolium*
Varietal Denomination: Gedi Three Ver

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 5 days.

(21) Appl. No.: 11/119,141

(22) Filed: Apr. 28, 2005

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

| | | | |
|---|---|---|---|
| PP10,463 | P | 6/1998 | Wain |
| PP13,455 | P2 | 1/2003 | Pieters |
| PP13,797 | P2 | 5/2003 | Pieters |

*Primary Examiner*—Kent Bell
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by distinctive bright yellow ray florets and a flat capitulum. The new variety has a round, spreading, flexible, free branching habit, and has medium to high vigor.

1 Drawing Sheet

Figure 1:
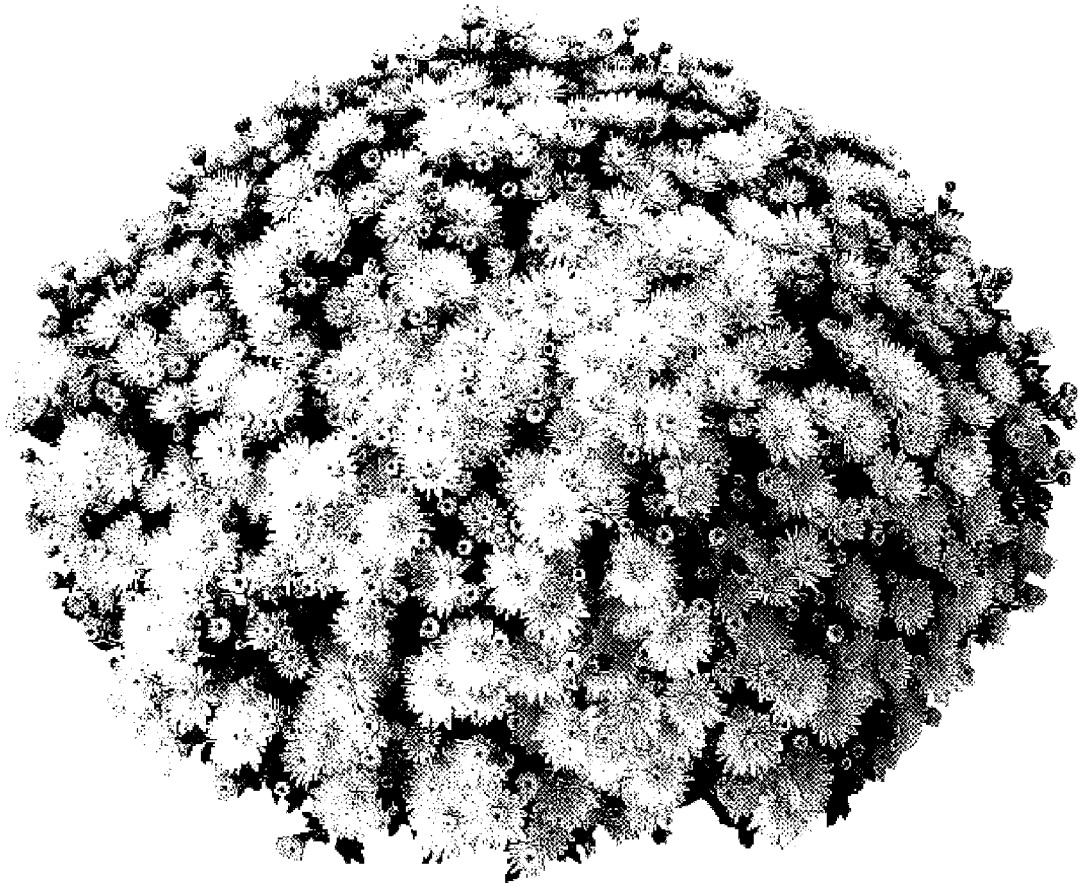

Latin name of the genus and species: *Crysanthemum morifolium.*
Variety denomination: 'Gedi Three Ver'.

BACKGROUND OF THE INVENTION

The new cultivar is a product of hybridization of a female parent *Chrysanthemum* plant variety 'Cleagar GF1' (U.S. Plant Pat. No. 10,463) and a male parent *Chrysanthemum* plant variety 'Draga' (unpatented, undistributed in the U.S.). The new cultivar was discovered and selected by Dirk Peters in a controlled environment in Oostnieuwkerke, Belgium, during September, 1999.

Asexual reproduction of the new cultivar 'Gedi Three Ver' by terminal cuttings and tissue culture was performed in Oxnard, Calif., and has shown that the unique features of this cultivar are stable and reproduced true to type on successive generations.

SUMMARY OF THE INVENTION

The cultivar 'Gedi Three Ver' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Ver.' These characteristics in combination distinguish 'Gedi Three Ver' as a new and distinct *Chrysanthemum* cultivar:

1. The flower has distinctive bright yellow ray florets and a flat capitulum.
2. The plant has a round, spreading habit.
3. The plant has a very free branching habit.
4. The plant exhibits medium to high vigor.
5. The plant is highly flexible and non-brittle.

Plants of the new cultivar 'Gedi Three Ver' are similar to plants of the female parent variety, 'Cleagar GF1' (U.S. Plant Pat. No. 10,463), in most horticultural characteristics. However, plants of the new cultivar have brighter, lighter yellow florets and a wider diameter flower than plants of the female parent variety. The new cultivar 'Gedi Three Ver' has an earlier natural season blooming response than the female parent variety. Additionally, plants of the new cultivar 'Gedi Three Ver' have a more round plant shape and are more freely branching in comparison to the female parent variety 'Cleagar GF1.'

Plants of the new cultivar 'Gedi Three Ver' are similar to plants of the male parent variety, 'Draga' (undistributed in the U.S.), in most horticultural characteristics. However, plants of the new cultivar have a flower that is larger in diameter, lighter, and brighter yellow than the flower of the male parent variety. Plants of the new cultivar 'Gedi Three Ver' also have a wider plant spread than the male parent variety. Additionally, the new cultivar has a natural season blooming response that is about two weeks earlier than the natural blooming response of the male parent variety 'Draga.'

In comparison to the commercially available variety 'GediI One Avi' (U.S. Plant Pat. No. 13,455), the new variety 'Gedi Three Ver' has a larger diameter flower with brighter yellow ray florets. The new variety 'Gedi Three Ver' has approximately 13 more flowers per flowering stem, and has fewer ray florets than the comparable variety 'Gedi One Avi.'

In comparison to the commercially available variety 'Gedi One Ces' (U.S. Plant Pat. No. 13,797), the new variety 'Gedi Three Ver' has lighter yellow ray florets, and fewer ray florets per flower. The new variety 'Gedi Three Ver' has about 10 more flowers per flowering stem than 'Gedi One Ces.' Additionally, the ray florets of new variety 'Gedi Three Ver' have an oblong shape.

BRIEF DESCRIPTION OF THE PHOTOGRAPH

The accompanying photograph in FIG. 1 illustrates in full color a typical plant of 'Gedi Three Ver' gorwn in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Ver' plants grown in a greenhouse in Oxnard, Calif., during the month of September, *2003*. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three Ver.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 28.5 cm.
Plant spread: Approximately 32 cm.
Growth rate: Moderate.
Branching characteristics: Free branching.
Length of lateral branches: Approximately 24 cm.
Number of leaves per lateral branch: Approximately 19.
Age of plant described: Approximately 135 days from a rooted cutting.

FOLIAGE

Leaf:
- *Arrangement.*—Alternate.
- *Average length.*—Approximately 5.8 cm.
- *Average width.*—Approximately 4.5 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 2.2 cm.
- *Color.*—Young foliage upper side: Near Green 137A. Young foliage under side: Near Green 137A. Mature foliage upper side: Near Green 137A. Mature foliage under side: Near Green 137A.
- *Leaf venation.*—Type: Palmately net. Venation color upper side: Near Green 138A. Venation color under side: Near Green 138A.

Petiole:
- *Average length.*—Approximately 1.8 cm.
- *Color.*—Near Green 138A.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Form.*—Decorative.
- *Natural flowering season.*—Approximately the last week of August through the first week of September.
- *Number of flowers per lateral branch.*—Approximately 25.
- *Diameter.*—Approximately 6.1 cm.
- *Depth.*—Approximately 2.1 cm.
- *Longevity on plant.*—Approximately 27 days.
- *Persistence.*—Persistent.

Ray florets:
- *Appearance.*—Matte.
- *Texture.*—Smooth.
- *Average number of ray florets per flower.*—Approximately 170.
- *Shape.*—Oblong.
- *Aspect.*—Flat.
- *Margin.*—Entire.
- *Apex.*—Retuse.
- *Length.*—Approximately 2.5 cm.
- *Width.*—Approximately 1 cm.
- *Color.*—Upper surface at first opening: Near Yellow 9A. Upper surface at maturity: Near Yellow 6A. Upper surface at fading: Near Yellow 8B. Under surface at first opening: Near Yellow 12A. Under surface at maturity: Near Yellow Yellow 9A. Under surface at fading: Near Yellow Yellow 6C.

Disc florets:
- *Appearance.*—Shiny.
- *Texture.*—Smooth.
- *Average number of disc florets per disc.*—Approximately 20.
- *Shape.*—Cylindric.
- *Apex.*—Obtuse.
- *Average length.*—Approximately 0.8 cm.
- *Average width.*—Approximately 0.1 cm.
- *Color.*—At first opening: Near Yellow 8B. At maturity: Near Yellow 12B. At fading: Near Yellow-orange 15D.

Peduncle:
- *Length.*—At terminal end (shortest): Approximately 3.1 cm. At lateral end (longest): Approximately 6.3 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Lightly pubescent.

Flower bud:
- *Length.*—Approximately 1 cm.
- *Diameter.*—Approximately 0.8 cm.
- *Form.*—Globular.
- *Color.*—Near Yellow 12B.

Involucral bracts (phyllaries):
- *Appearance.*—Matte.
- *Texture.*—Lightly pubescent.
- *Number.*—Approximately 36.
- *Shape.*—Oblanceolate.
- *Margin.*—Entire.
- *Apex.*—Acute.
- *Length.*—Approximately 1 cm.

*Width.*—Approximately 0.9 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 7A.
*Style color.*—Near Yellow 4D.
*Style length.*—Approximately 0.9 cm.
*Stamens.*—Absent.

Disc florets:
*Number of pistils per floret.*—1.
*Stigma shape.*—Two-branched.
*Stigma color.*—Near Yellow 7D.
*Style length.*—Approximately 0.3 cm.
*Style color.*—Near Yellow 4C.
*Number of stamens per floret.*—Approximately 5.
*Anther shape.*—Tubular.
*Anther color.*—Near Yellow 12A.
*Pollen color.*—Near Yellow 12A.

OTHER CHARACTERISTICS

Disease resistance: Neither resistance nor susceptibility has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of about 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Ver' as herein illustrated and described.

* * * * *